(12) United States Patent
Hölzl et al.

(10) Patent No.: US 6,346,260 B1
(45) Date of Patent: Feb. 12, 2002

(54) MICROBICIDAL ACTIVE INGREDIENTS

(75) Inventors: Werner Hölzl, Eschentzwiller (FR); Wolfgang Haap, Grenzach-Wyhlen (DE); Dietmar Ochs, Schopfheim (DE); Karin Puchtler, Fischingen (DE); Marcel Schnyder, Birsfelden (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/629,416

(22) Filed: Aug. 1, 2000

(30) Foreign Application Priority Data

Aug. 6, 1999 (EP) ............................................ 99810708

(51) Int. Cl.⁷ ..................... A01N 43/40; A01N 35/04; C01D 213/04; C07C 49/83
(52) U.S. Cl. ..................... 424/404; 546/315; 568/331; 568/337; 544/224
(58) Field of Search .............................. 424/404, 401; 568/337, 331; 514/689, 685, 355; 546/315; 544/224

(56) References Cited

U.S. PATENT DOCUMENTS 4,814,162 A * 3/1989 Lang et al. ..................... 424/47

OTHER PUBLICATIONS

Ahluwalia, V.K. et al. : Synthesis and antimicrobial activities of some new—pyrazoles. Indian J. Chem. vol. 28B, pp. 150–153, Feb. 1989.*

K. A. Thakar et al., "Synthesis of Fural Analogs of Substituted Flavonoids", Journal of the Indian Chemical Society, 50(3), pp. 420–423 (1973).

K. A. Thakar et al., "Synthesis and Screening of Some 1, 3–Propane Diones and Flavones", Journal of the Indian Chemical Society, 60(7), pp. 668–670 (1983).

* cited by examiner

Primary Examiner—Charanjit S. Aulakh
(74) Attorney, Agent, or Firm—Kevin T. Mansfield

(57) ABSTRACT

The use of hydroxyphenyl-1,3-propanediones of formula:

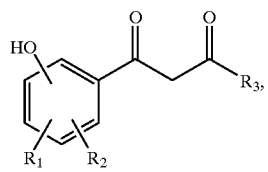

(1)

wherein $R_1$ and $R_2$ are each independently of the other hydrogen, $C_1$–$C_{12}$alkyl, $C_1$–$C_{12}$alkoxy, trifluoro-$C_1$–$C_3$alkyl, phenyl or halogen;

$R_3$ is a 5- or 6-membered heteroaromatic radical; thiophenyl; or a radical of formula:

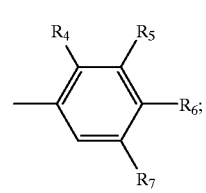

(1a)

$R_4$, $R_5$, $R_6$ and $R_7$ are each independently of the other hydrogen, halogen, $C_1$–$C_{12}$alkyl, $C_1$–$C_{12}$alkoxy, carboxy or trifluoro-$C_1$–$C_3$alkyl;

in the antimicrobial treatment of surfaces, is described.

The compounds exhibit a pronounced action against pathogenic gram-positive and gram-negative bacteria, and also against yeasts and molds.

13 Claims, No Drawings

MICROBICIDAL ACTIVE INGREDIENTS

The present invention relates to the use of hydroxyphenyl-1,3-propanediones in the anti-microbial treatment of surfaces.

The hydroxyphenyl-1,3-propanediones used according to the invention correspond to formula:

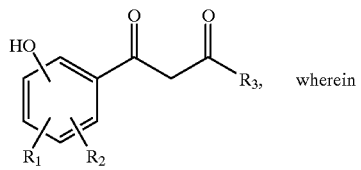

(1)

wherein $R_1$ and $R_2$ are each independently of the other hydrogen, $C_1$–$C_{12}$alkyl, $C_1$–$C_{12}$alkoxy, trifluoro-$C_1$–$C_3$alkyl, phenyl or halogen;

$R_3$ is a 5- or 6-membered heteroaromatic radical; thiophenyl; or a radical of formula:

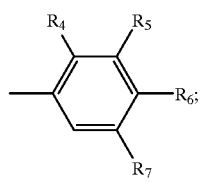

(1a)

$R_4$, $R_5$, $R_6$ and $R_7$ are each independently of the other hydrogen, halogen, $C_1$–$C_{12}$alkyl, $C_1$–$C_{12}$alkoxy, carboxy or trifluoro-$C_1$–$C_3$alkyl.

$C_1$–$C_{12}$Alkyl and $C_1$–$C_{12}$alkoxy are straight-chain or branched alkyl and alkoxy radicals, for example methyl, ethyl, n-propyl, isopropyl, n-butyl, sec-butyl, tert-butyl, amyl, isoamyl or tert-amyl, heptyl, octyl, isooctyl, nonyl, decyl, undecyl and dodecyl, and methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy and dodecyloxy.

Preferred 6-membered heteroaromatic radicals are pyrazinyl, pyrimidinyl and pyridazinyl and especially pyridyl.

Examples of 5-membered heteroaromatic radicals are thienyl, furyl, pyrrolyl, imidazolyl, pyrazolyl, isoxazolyl and furazanyl.

The 5- or 6-membered heteroaromatic radicals may be unsubstituted or substituted by halogen, such as chlorine or bromine, by nitro, by $C_1$–$C_5$alkyl or by $C_1$–$C_5$alkoxy.

There are preferably used also compounds of formula:

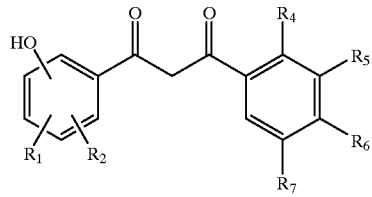

(2)

wherein $R_1$, $R_2$, $R_3$, $R_4$, $R_5$, $R_6$ and $R_7$ are as defined for formula (1).

Examples of compounds that can be used according to the invention correspond to formulae:

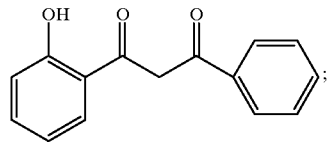

(3)

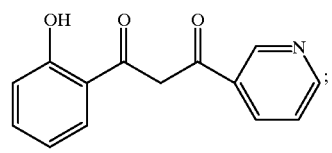

(4)

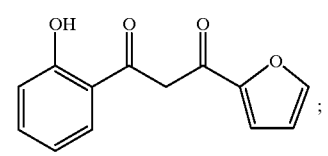

(5)

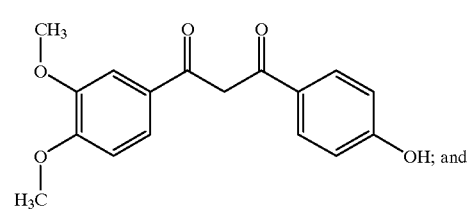

(6)

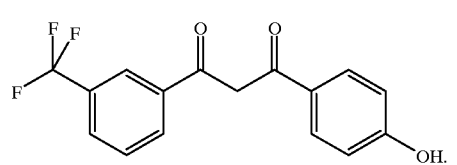

(7)

The preparation of the compounds of formula (1) is carried out in a manner known per se in analogy to K. A. Thakar, D. D. Goswami, G. G. Pachpor, J.Ind.Chem.Soc. (I) (1973), 420–423 in a two-step reaction in accordance with the following scheme:

1st Step

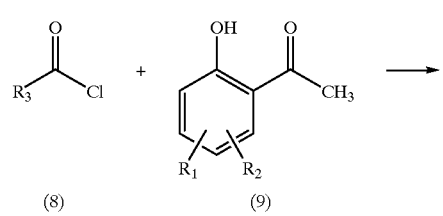

(8)        (9)

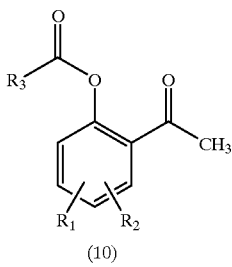

(10)

2nd Step

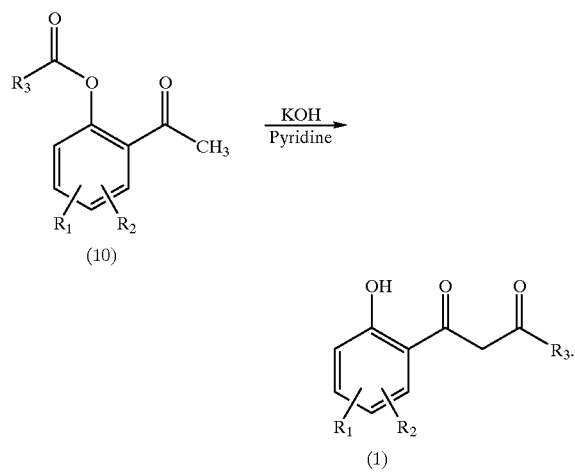

The invention relates also to the process for the preparation of the compounds according to formula (1).

The process is carried out in a suitable solvent, usually at a temperature of from 0 to 50° C. (1st step).

Preferably, pyridine is used as solvent at a temperature of 25° C.

In a 2nd step the ester of formula (10) is rearranged to form the corresponding target compound of formula (1) by reaction with KOH powder in a suitable solvent, preferably pyridine, at a temperature of from 40 to 80° C., preferably 50° C.

A further process for the preparation of the compounds of formula (1) is solid phase synthesis on polymeric supports.

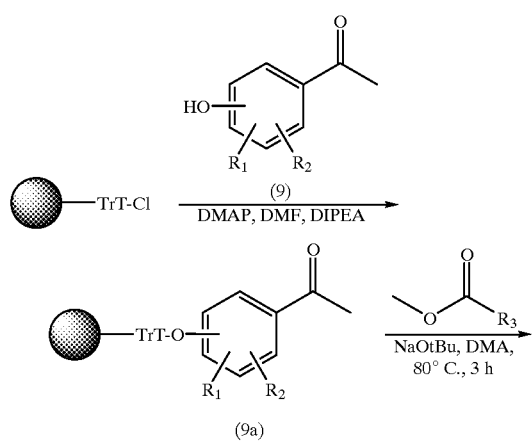

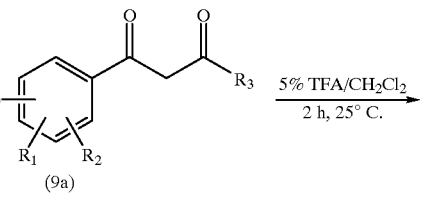

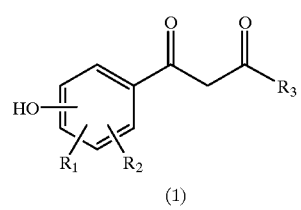

For that purpose, $R_1$- and $R_2$-substituted hydroxyacetophenones of formula (9) are immobilised on a polystyrene-trityl chloride resin using suitable solvents, bases and catalysts, preferably dimethylformamide, N,N-diisopropylethylamine and 4-(N,N-dimethylamino)pyridine.

$R_3$-Substituted esters are then heated with the polystyrene resin using suitable bases and solvents at temperatures of from 40 to 100° C.

Preferably, sodium tert-butanolate and N,N-dimethylacetamide are used at a temperature of 80° C.

For the removal of the compounds according to formula (1), the resins are treated with 5% trifluoroacetic acid in dichloromethane.

Some of the hydroxyphenyl-1,3-propanediones used according to the invention are known compounds, while some are new compounds.

The new compounds correspond to formula:

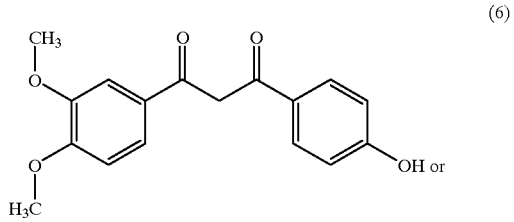

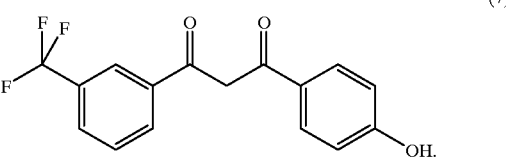

The hydroxyphenyl-1,3-propanediones used according to the invention exhibit a pronounced antimicrobial action, especially against pathogenic gram-positive and gram-negative bacteria and also against bacteria of skin flora, e.g. Corynebacterium xerosis (bacteria that cause body odour), and also against yeasts and moulds. They are therefore especially suitable in the disinfection, deodorisation and general antimicrobial treatment of the skin and mucosa and of integumentary appendages (hair), more especially in the disinfection of the hands and of wounds.

They are therefore suitable as antimicrobial active ingredients in personal care preparations, for example shampoos, bath additives, hair-care products, liquid and solid soaps (based on synthetic surfactants and salts of saturated and/or unsaturated fatty acids), lotions and creams, deodorants, other aqueous or alcoholic solutions, e.g. cleansing solutions for the skin, moist cleansing cloths, oils or powders.

The invention therefore relates also to a personal care preparation comprising at least one compound of formula (1) as well as cosmetically tolerable carriers or adjuvants.

The personal care preparation according to the invention comprises from 0.01 to 15% by weight, preferably from 0.5 to 10% by weight, based on the total weight of the composition, of the hydroxyphenyl-1,3-propanedione compound of formula (1) and cosmetically tolerable adjuvants.

Depending upon the form of the personal care preparation, it will comprise, in addition to the hydroxyphenyl-1,3-propanedione compound of formula (1), further constituents, for example sequestering agents, colourings, perfume oils, thickening or solidifying (consistency regulator) agents, emolients, UV absorbers, skin-protective agents, antioxidants, additives that improve mechanical properties, such as dicarboxylic acids and/or Al, Zn, Ca and Mg salts of $C_{14}$–$C_{22}$ fatty acids, and optionally additional preservatives and antimicrobial active ingredients.

The personal care preparation according to the invention may be formulated as a water-in-oil or oil-in-water emulsion, as an alcoholic or alcohol-containing formulation, as a vesicular dispersion of an ionic or non-ionic amphiphilic lipid, as a gel, a solid stick or as an aerosol formulation.

A water-in-oil or oil-in-water emulsion containing the hydroxyphenyl-1,3-propanedione compound of formula (1) comprises as cosmetically tolerable adjuvants preferably from 5 to 50% of an oily phase, from 5 to 20% of an emulsifier and from 30 to 90% water.

The oily phase may contain any oil suitable for cosmetic formulations, e.g. one or more hydrocarbon oils, a wax, a natural oil, a silicone oil, a fatty acid ester or a fatty alcohol. Preferred mono- or poly-ols are ethanol, isopropanol, propylene glycol, hexylene glycol, glycerol and sorbitol.

Compounds according to the invention may be contained in a variety of cosmetic preparations. Especially the following preparations, for example, come into consideration:

skin-care preparations, e.g. skin-washing and cleansing preparations in the form of tablet-form or liquid soaps, soapless detergents or washing pastes;

bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams, lip-care preparations, e.g. lipsticks, lip gloss, lip contour pencils, nail-care preparations, such as nail varnish, nail varnish removers, nail hardeners or nail hardener removers;

intimate hygiene preparations, e.g. intimate washing lotions or intimate sprays;

foot-care preparations, e.g. foot baths, foot powders, foot creams or foot balsams, special deodorants and antiperspirants or callous-removing preparations;

light-protective preparations, such as sun milks, lotions, creams and oils, sun blocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. soapless detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or after-shave lotions;

fragrance preparations, e.g. fragrances (eau de Cologne, eau de toilette, eau de parfum, parfum de toilette, perfume), perfume oils or cream perfumes;

dental-care, denture-care and mouth-care preparations, e.g. toothpastes, gel tooth-pastes, tooth powders, mouthwash concentrates, anti-plaque mouthwashes, denture cleaners or denture fixatives;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, foams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

An antimicrobial soap has, for example, the following composition:

0.01 to 5% by weight of the compound of formula (1)

0.3 to 1% by weight titanium dioxide 1 to 10% by weight stearic acid ad 100% soap base, e.g. the sodium salts of tallow fatty acid and coconut fatty acid or glycerol.

A shampoo has, for example, the following composition:

0.01 to 5% by weight of the compound of formula (1)

12.0% by weight sodium laureth-2-sulfate 4.0% by weight cocamidopropyl betaine 3.0% by weight NaCl and water ad 100%.

A deodorant has, for example, the following composition:

0.01 to 5% by weight of the compound of formula (1)

60% by weight ethanol 0.3% by weight perfume oil and water ad 100%.

Example of an O/W emulsion:

0.01–5% by weight of the compound of formula (1)

12% by weight glyceryl stearate
6% by weight paraffin oil
6% by weight caprylic/capric triglyceride
4% by weight glycerol
0.2% by weight disodium EDTA
1.0% by weight citric acid (20%) and
65.8–70.8% by weight water.
Example of an O/W emulsion:
0.01–5% by weight of the compound of formula (1)
3.5% by weight PEG-30 dipolyhydroxystearate
10.0% by weight paraffin oil
4% by weight caprylic/capric triglyceride
4% by weight dicaprylic ether
0.2% by weight disodium EDTA
3.4% by weight glycerol and
69.9–74.9% by weight water.

The invention relates also to an oral care composition, comprising
   0.01 to 15% by weight, based on the total weight of the composition, of the compound of formula (1) and orally tolerable adjuvants.
Example of an oral care composition:
10% by weight sorbitol
10% by weight glycerol
15% by weight ethanol
15% by weight propylene glycol
0.5% by weight sodium lauryl sulfate
0.25% by weight sodium methylcocyl taurate
0.25% by weight polyoxypropylene polyoxyethylene block copolymer
0.10% by weight peppermint flavouring
0.1 to 0.5% by weight of a compound of formula (1) and
48.6% by weight water.

The oral care composition according to the invention may be, for example, in the form of a gel, a paste, a cream or an aqueous preparation (mouthwash).

The oral care composition according to the invention may also comprise compounds that release fluoride ions which are effective against the formation of caries, for example inorganic fluoride salts, e.g. sodium, potassium, ammonium or calcium fluoride, or organic fluoride salts, e.g. amine fluorides, which are known under the trade name Olafluor.

The hydroxyphenyl-1,3-propanediones of formula (1) used according to the invention are also suitable for the antimicrobial treatment of textile fibre materials. Such materials are undyed and dyed or printed fibre materials, e.g. of silk, wool, polyamide, polyester, poly-propylene or polyurethanes, and especially cellulose-containing fibre materials of all kinds. Such fibre materials are, for example, natural cellulose fibres, such as cotton, linen, jute and hemp, as well as cellulose and regenerated cellulose. Preferred suitable textile fibre materials are made of cotton.

The compounds of formula (1) are also suitable, alone or in combination with other antimicrobial substances, for preserving cosmetic products, e.g. shampoos, bath additives, hair-care preparations, liquid and solid soaps (based on synthetic surfactants and salts of saturated and/or unsaturated fatty acids), lotions and creams, deodorants, other aqueous or alcoholic solutions, e.g. cleansing solutions for the skin, moist cleansing cloths, oils or powders and household products, for example in washing and cleaning formulations, e.g. in liquid or powder washing agents or softeners.

The hydroxyphenyl-1,3-propanediones used according to the invention are also suitable for imparting antimicrobial properties to plastics, e.g. polyethylene, polypropylene, polyurethane, polyester, polyamide, polycarbonate, latex etc. Fields of use therefor are, for example, floor coverings, plastics coatings, plastics container and packaging materials, kitchen and bathroom utensils (e.g. brushes, shower curtains, sponges, bathmats), latex filter materials (air and water filters), plastics articles used in the field of medicine, e.g. dressing materials, syringes, catheters etc., so-called "medical devices", gloves and mattresses.

Paper, for example papers used for hygiene purposes, may also be provided with antimicrobial properties using the hydroxyphenyl-1,3-propanediones according to the invention.

It is also possible for nonwovens, e.g. nappies/diapers, sanitary towels, panty liners, and cloths for hygiene and household uses, to be provided with antimicrobial properties in accordance with the invention.

The hydroxyphenyl-1,3-propanediones can be used especially also in household and all-purpose cleaners for cleaning and disinfecting hard surfaces.

A cleaning preparation has, for example, the following composition:

0.01 to 5% of the compound of formula (1)

3.0% octyl alcohol 4EO 1.3% fatty alcohol $C_8$–$C_{10}$ polyglucoside 3.0% isopropanol ad 100% water.

In addition to preserving cosmetic and household products, technical products, such as paper treatment liquors, printing thickeners of starch or of cellulose derivatives, varnishes and paints, can be preserved and provided with antimicrobial properties.

The hydroxyphenyl-1,3-propanediones of formula (1) are also suitable for the antimicrobial treatment of wood and for the antimicrobial treatment of leather and the provision of leather with antimicrobial properties.

The compounds according to the invention are also suitable for the protection of cosmetic products and household products from microbial damage.

The following Examples serve to illustrate the invention but do not limit the invention to the Examples.

EXAMPLE 1

Preparation of the Compound of Formula

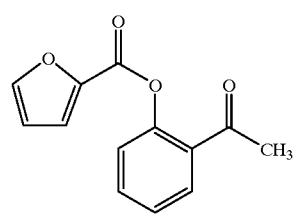

(101a)

Reaction Scheme

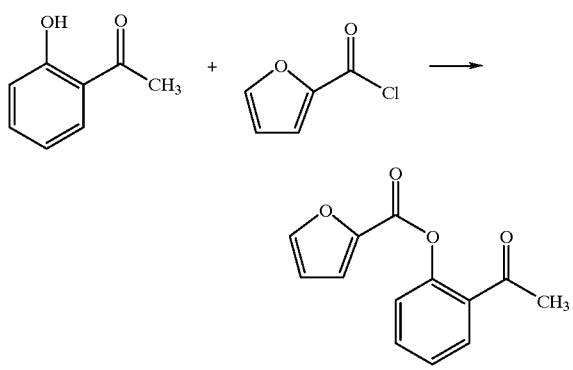

2-Hydroxyacetophenone (0.5 mol; 68.1 g) is dissolved in pyridine (121 ml) at 25° C. 2-Furoyl chloride (0.51 mol, 66.6 g) is then added in the course of 10 minutes, the temperature rising to a maximum of 50° C. The mixture is then cooled to 25° C. and stirred for 1.5 hours. The thick reaction mass is poured into aqueous HCl solution (10%, 1 litre) at from 5 to 20° C., and the white product is filtered off and washed with water (100 ml).

The o-(2-furoyloxy)acetophenone crude product is recrystallised from ethanol (200 ml). The crystals are dried in vacuo.

Yield: 108.4 g (94.2% of theory)

EXAMPLE 2
Preparation of the Compound of Formula

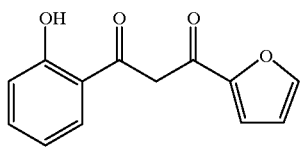

(101)

2-(2-Furoyloxy)acetophenone (0.43 mol; 100 g) is dissolved in pyridine (260 ml). The mixture is heated to from 45 to 50° C. KOH powder (0.52 mol; 29 g) is then added in the course of 10 minutes and the mixture is stirred with pyridine (100 ml). The reaction mixture is then stirred at 45° C. for 15 minutes, and ethyl acetate (1.3 litres) is added until the pH value falls to <7. The reaction mixture is then cooled to 10° C., a yellow product being precipitated. The precipitate is filtered off, washed with water (100 ml) and recrystallised from ethanol/water (3:1, 500 ml). The crystals are dried in vacuo.

Yield: 60.6 g (60.6% of theory)

EXAMPLE 3
Solid Phase Synthesis of the Compound of Formula

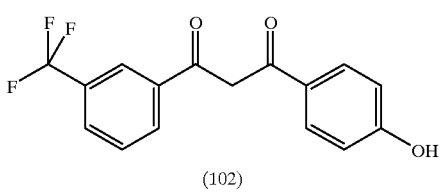

(102)

-continued
Reaction scheme:

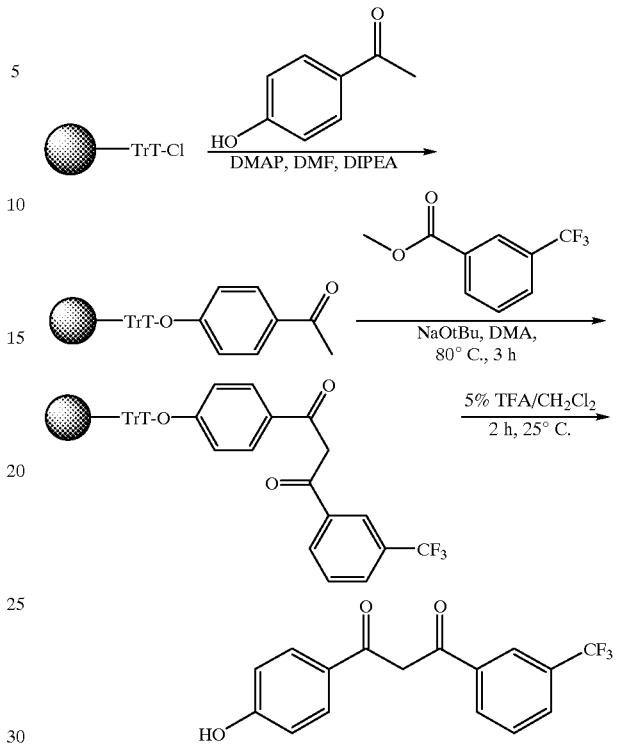

Polystyrene-trityl chloride resin (100 mg, loading approx. 1 mmol/g) is shaken at 25° C. for 18 hours with 4-hydroxyacetophenone (10 eq), DIPEA (10 eq) and DMAP (catalytic amounts) in DMF (2 ml). The resin is then filtered off with suction and washed intensively with DMF (3×), methanol (3×), DCM (3×) and methanol (3×) and dried in vacuo.

The IR spectrum exhibits a C(=O) bond-stretching vibration at 1655 cm$^{-1}$.

For the Claisen condensation, the loaded resin (100 mg) is heated at 80° C. for 3 hours with 3-trifluoromethylbenzoic acid methyl ester (10 eq) and sodium tert-butanolate (10 eq) in DMA (2 ml, absolute). The resin is then filtered off with suction, washed as described above and dried in vacuo.

For removal, the resin (100 mg) is shaken at 25° C. for 2 hours with 5% TFA in dichloromethane (2 ml), and then the removal solution is concentrated to dryness by evaporation and freeze-dried from tert-butyl alcohol/water (4:1).

Yield: 52.3%

EXAMPLE 4
Preparation of a Liquid Washing Agent

| | |
|---|---|
| 0.01–5% | of the compound of formula (101) |
| 15.0% | PEG-7 $C_4$–$C_{15}$alcohol ether |
| 10.0% | sodium dodecylbenzenesulfonate |
| 10.0% | propylene glycol |
| 3.0% | sodium citrate |
| ad 100% | deionised water |

The compound of formula (101) is dissolved in the $C_{14}$–$C_{15}$alcohol ether at 50° C. Propylene glycol and sodium dodecylbenzenesulfonate are added and the mixture is stirred until homogeneous. After cooling to 22° C., sodium citrate and water are added.

EXAMPLE 5

Preparation of a Softener

| | |
|---|---|
| 0–5% | of the compound of formula (101) |
| 4.0% | of the compound of formula $\left[\begin{array}{c} \text{CH}_3 \\ | \\ \text{R}-\text{N}^+-\text{R} \\ | \\ \text{CH}_3 \end{array}\right]$ Cl$^-$ |
| 0.5% | R = aliphatic radical of tallow fatty acid pareth-25-7 and |
| ad 100% | deionised water. |

The compound of formula (101) is dissolved in Quaternium 18 at 40° C.; pareth-25-7 and water are added and the mixture is stirred until a homogeneous mixture is formed.

EXAMPLE 6

Preparation of a Dishwashing Agent

| | |
|---|---|
| 0.01–5 | of the compound of formula (101) |
| 7.0% | sodium lauryl sulfate |
| 7.0% | sodium myreth sulfate |
| 4.0% | lauryl glucoside |
| 1.1% | cocobetaine |
| 5.0% | ethanol |
| 1.0% | citric acid |
| ad 100% | deionised water |

The compound of formula (101) is dissolved in ethanol. The surfactants (sodium lauryl sulfate, sodium myreth sulfate, lauryl glucoside and cocobetaine) are added predissolved in water and the mixture is stirred at 40° C. until homogeneous. Citric acid and water are added to the solution at 22° C.

EXAMPLE 7

Preparation of a Liquid Soap

| | |
|---|---|
| 0.01–5% | of the compound of formula (101) |
| 10.0% | sodium laureth-2-sulfate |
| 3.0% | cocamidopropyl betaine |
| 2.0% | lauryl glucoside |
| 1.0% | glycol distearate |
| 1.0% | sodium chloride |
| ad 100% | deionised water. |

The compound of formula (101) is solubilised at 50° C., with stirring, in cocamidopropyl betaine and lauryl glucoside. Sodium laureth-2-sulfate and glycol distearate are added and the mixture is stirred at 50° C. until homogeneous. When the glycol distearate has fully dissolved, the mixture is cooled to room temperature, with stirring; water is added and the viscosity is adjusted with sodium chloride.

EXAMPLE 8

Preparation of a Surface Disinfectant 0.01 to 5% of the compound of formula (101)
3.0% octyl alcohol 4EO
1.3% fatty alcohol $C_8$–$C_{10}$polyglucoside
3.0% isopropanol
ad 100% water The compound of formula (101) is dissolved in isopropanol; octyl alcohol 4EO and fatty alcohol $C_8$–$C_{10}$polyglucoside are added to the solution and the mixture is stirred until homogeneous. The pH value is adjusted with ethanolamine and the formulation is made up to 100% with water.

EXAMPLE 9

Determination of Antimicrobial Activity in Accordance with the Microtitre Plate Method Determination of the Minimum Inhibitory Concentration (MIC value) in Microtitre Plates Nutrient Medium casein-soybean flour-peptone bouillon for the preparation of the precultures of the test bacteria and yeast.

Mycological slant agar for the preculture of moulds.

Examples of Test Organisms

Bacteria

*Staphylococcus hominis* DSM 20328

*Escherichia coli* NCTC 8196

*Pseudomonas aeruginosa* CIP A-22

*Staphylococcus aureus* ATCC 9144

*Corynebacterium xerosis* ATCC 373

Yeast

*Candida albicans* ATCC 10231

Mould

*Aspergillus niger* ATCC 6275

*Rhizopus stolonifer* DSM 63011

*Penicillium expansum* ATCC 36200

Procedure

The test substances are predissolved in dimethyl sulfoxide (DMSO) and tested in a dilution series of 1:2.

Bacteria and yeast are cultured overnight in CASO bouillon, the mould on mycological slant agar and rinsed off with 10 ml of 0.85% sodium chloride solution (+0.1% TritonX-100).

All test organisms are adjusted to an organism count of 1–5*10$^6$ CFU/ml with 0.85% sodium chloride solution.

The test substances are prepipetted into microtitre plates in an amount of 8 μl per well.

Previously diluted test organism suspensions are diluted 1:100 in CASO bouillon (bacteria and yeast) and Sabouraud 2% glucose bouillon (mould) and added to the test substances in an amount of 192 μl per well.

The test batches are incubated for 48 hours at 37° C. (bacteria and yeast) or for 5 days at 28° C. (mould).

After incubation, the growth is determined by reference to the turbidity of the test batches (optical density) at 620 nm in a microplate reader.

The minimum inhibitory concentration (MIC value) is the concentration of substance at which (compared with the growth of the control) an appreciable inhibition of the growth ($\leq$20% growth) of the test organisms is ascertained.

One microtitre plate is used for each test organism and substance concentration.

All substances are tested in duplicate.

The results obtained (MIC in ppm) are given in Table 1 and 2.

TABLE 1

Compound of formula (101)

| Microorganism | | [ppm] |
|---|---|---|
| *Staphylococcus aureus* | ATCC 9144 | 100–500 |
| *Corynebacterium xerosis* | ATCC 373 | 50 |
| *Escherichia coli* | NCTC 8196 | 50 |
| *Pseudomonas aeruginosa* | CIP A-22 | >1000 |
| *Candida albicans* | ATCC 10231 | >100–500 |

TABLE 1-continued

Compound of formula (101)

| Microorganism | | [ppm] |
|---|---|---|
| *Aspergillus niger* | ATCC 6275 | 100 |
| *Rhizopus stolonifer* | DSM 63011 | 50 |
| *Penicillium expansum* | ATCC 36200 | 100 |

TABLE 2

| Compound | | SH | EC | PA | CA | AN |
|---|---|---|---|---|---|---|
| (103) | [thiophene-C(O)-CH2-C(O)-C6H4-OH] | >120 | >120 | >120 | >120 | >120 |
| (104) | [pyridine-C(O)-CH2-C(O)-C6H4-OH] | — | — | — | — | — |
| (105) | [2-OCH3-C6H4-C(O)-CH2-C(O)-C6H4-OH] | >120 | >120 | >120 | >120 | >120 |
| (106) | [2-CH3-C6H4-C(O)-CH2-C(O)-C6H4-OH] | >120 | >120 | >120 | >120 | >120 |
| (107) | [3,4-(OCH3)2-C6H3-C(O)-CH2-C(O)-C6H4-OH] | >120 | 120 | >120 | >120 | 120 |
| (108) | [3,4,5-(OCH3)3-C6H2-C(O)-CH2-C(O)-C6H4-OH] | >120 | >120 | >120 | >120 | >120 |

TABLE 2-continued

| Compound | Test organisms | | | | |
|---|---|---|---|---|---|
| | SH | EC | PA | CA | AN |
| (109) methyl 3-(3-(4-hydroxyphenyl)-3-oxopropanoyl)benzoate | >120 | >120 | >120 | >120 | >120 |
| (110) 1-(4-hydroxyphenyl)-3-(3-(trifluoromethyl)phenyl)propane-1,3-dione | >120 | 60 | >120 | >120 | 60 |
| (111) 1-(4-hydroxyphenyl)-3-phenylpropane-1,3-dione | >120 | >120 | >120 | >120 | >120 |
| (112) 1-(2-hydroxy-5-methylphenyl)-3-phenylpropane-1,3-dione | >120 | >120 | >120 | >120 | >120 |
| (113) 1-(5-chloro-2-hydroxy-4-methylphenyl)-3-phenylpropane-1,3-dione | >120 | >120 | >120 | >120 | >120 |
| (114) 1-(5-bromo-2-hydroxyphenyl)-3-phenylpropane-1,3-dione | >120 | >120 | >120 | >120 | >120 |
| (115) 1-(2-hydroxyphenyl)-3-phenylpropane-1,3-dione | >120 | >120 | >120 | >120 | >120 |

--- = not determined
Abbreviations:
SH = *Staphylococcus hominis* DSM 20368
EC = *Escherichia coli* NCTC 8196
PA = *Pseudomonas aeruginosa* CIP-A 22
CA = *Candida albicans* ATCC 10231
AN = *Aspergillus niger* ATCC 6275

What is claimed is:

1. A method for the antimicrobial treatment of surfaces comprising applying to the surface a compound of formula:

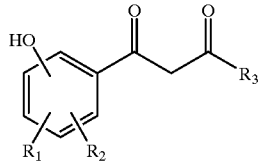

wherein
$R_1$ and $R_2$ are each independently of the other hydrogen, $C_1$–$C_{12}$alkyl, $C_1$–$C_{12}$alkoxy, trifluoro-$C_1$–$C_3$alkyl, phenyl or halogen;
$R_3$ is a 6-membered heteroaromatic radical selected from pyridyl, pyrazinyl, pyrimidinyl and pyridazinyl; or a compound of formula:

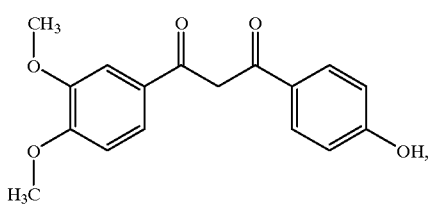

or a compound formula:

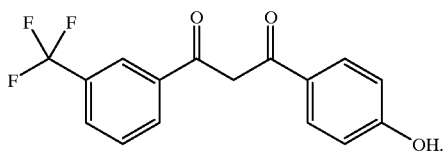

2. A method according to claim 1, wherein $R_3$ is pyridyl.

3. A method according to claim 2, wherein the compound is a compound of formula

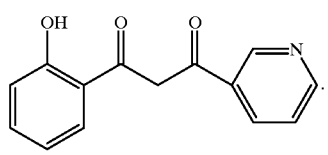

4. A process for the preparation of a compound of formula (1) according to claim 1, which process comprises immobilising the hydroxyacetophenone compound of formula (9) on a polystyrene-trichloride resin using suitable solvents, bases and catalysts and heating the resulting ester of formula (9a) with polystyrene resin using suitable bases and solvents at a temperature of from 40 to 100° C. and, for the removal of the compound of formula (1), treating the resins with 5% trifluoroacetic acid in dichloromethane in accordance with the following scheme:

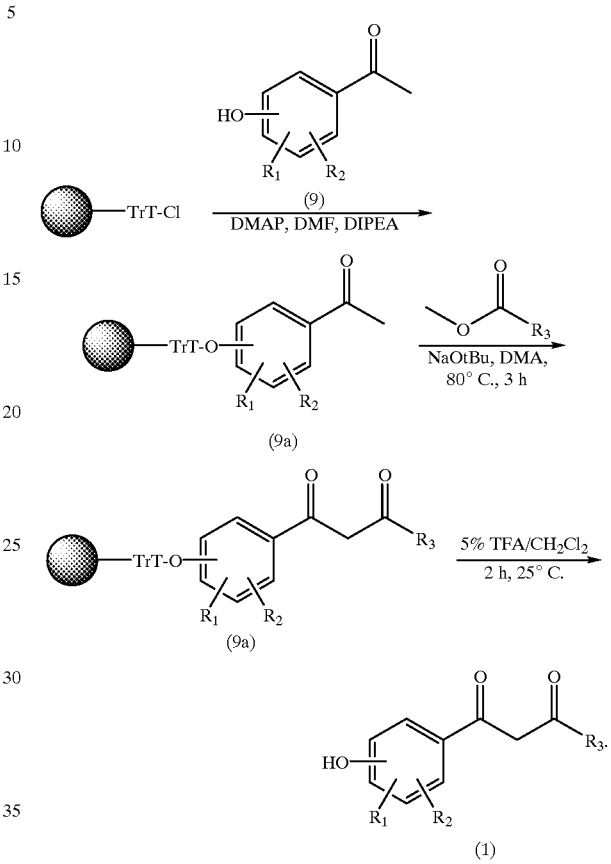

5. A method for the antimicrobial treatment of the skin, mucosa and hair comprising applying to the skin, mucosa and hair a compound of formula (1), (5) or (6) according to claim 1.

6. A method for the antimicrobial treatment of textile fibre materials comprising applying to the textile fibre materials a compound of formula (1), (5) or (6) according to claim 1.

7. A method for the antimicrobial treatment of plastics, paper, nonwovens and leather comprising treating the leather with a compound of formula (1), (5) or (6) according to claim 1.

8. A method for the preservation of cosmetic products comprising applying to said products a compound of formula (1), (5) or (6) according to claim 1.

9. A personal care preparation, comprising
from 0.01 to 15% by weight, based on the total weight of the composition, of a compound of formula (1), (5) or (6) and cosmetically tolerable adjuvants according to claim 1.

10. An oral care composition, comprising
from 0.01 to 15% by weight, based on the total weight of the composition, of a compound of formula (1), (5) or (6) according to claim 1 and orally tolerable adjuvants.

11. A compound of formula:

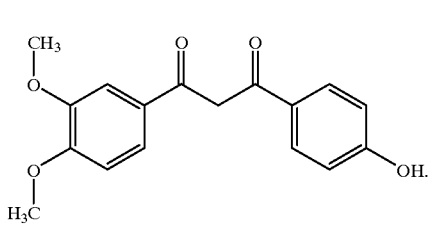

(6)

12. A compound of formula:

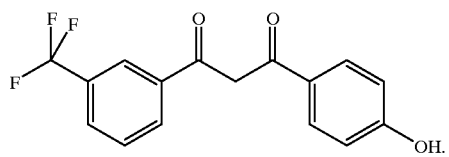

(7)

13. A process for the preparation of a compound of formula (1) according to claim 1, which process comprises reacting an acid chloride of formula (8) with a hydroxyacetophenone compound of formula (9) in a suitable solvent (1st reaction step) and reacting the resulting ester of formula (10) with KOH to form a compound of formula (1) (2nd reaction step) in accordance with the following scheme:

1st step:

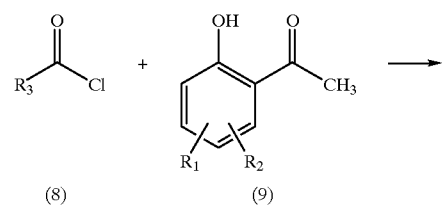

(8)      (9)

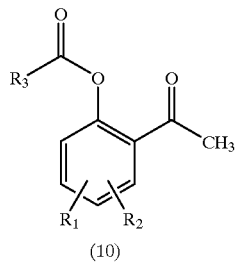

(10)

2nd step:

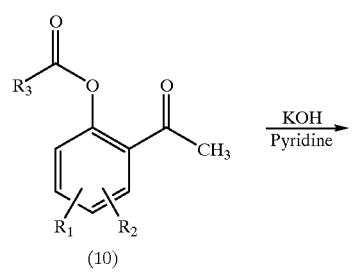

(10)

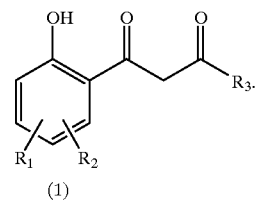

(1)

* * * * *